United States Patent
Paulson et al.

(10) Patent No.: US 6,375,865 B1
(45) Date of Patent: Apr. 23, 2002

(54) ELECTRIC-ARC RESISTANT COMPOSITION

(75) Inventors: Roy Victor Paulson, Temecula, CA (US); Elihu Hoagland, IV, Louisville, KY (US)

(73) Assignee: Paulson Manufacturing Corporation, Temecula, CA (US)

(*) Notice: Subject to any disclaimer, the term of this patent is extended or adjusted under 35 U.S.C. 154(b) by 0 days.

(21) Appl. No.: 09/372,371

(22) Filed: Aug. 11, 1999

(51) Int. Cl.[7] .................................................. H01B 1/00
(52) U.S. Cl. .............................. 252/500; 8/506; 8/637.1; D29/108; D29/109; D29/110; 2/410; 2/426; 2/424; 2/431; 2/434
(58) Field of Search .............................. 252/500; 8/506, 8/637.1; D29/108, 109, 110; 2/426, 410, 424, 431, 434

(56) References Cited

U.S. PATENT DOCUMENTS

| | | | |
|---|---|---|---|
| 4,176,098 A | 11/1979 | Needham | 260/18 R |
| 4,631,214 A | * 12/1986 | Hasegawa | 428/68 |
| 4,935,166 A | * 6/1990 | Lee et al. | 252/582 |
| 5,008,317 A | 4/1991 | Wolfer | 524/262 |
| 5,223,334 A | 6/1993 | Green | 428/225 |
| 5,359,174 A | * 10/1994 | Smith et al. | 200/144 |

OTHER PUBLICATIONS

American Society for Testing and Materials, "Provisional Standard Test Method for Determining Ignitability of Clothing by Electric Arc Exposure Method Using a Mannequin," Designation: PS 57–97, pp. 1–7, (1997).

American Society for Testing and Materials, "Provisional Standard Test Method for Determining Arc Thermal Performance (Value) of Textile Materials for Clothing by Electric Arc Exposure Method Using Instrumented Sensor Panels," Designation: PS 58–97, pp. 1–11, (1997).

R.L. Doughty, "Predicting Incident Energy to Better Manage the Electric Arc Hazard on 600 V Power Distribution Systems," IEEE, Paper No. PCIC–98–36, pp. 329–346, (1998).

S. Jamil, "Arc and Flash Burn Hazards at Various Levels of an Electrical System," IEEE Transactions on Industry Applications, vol. 33, No. 2, pp.359–366, (1997).

R.H. Lee, "The Other Electrical Hazard Electric Arc Blast Burns," IEEE, pp. 401–406, (1981).

T.E. Neal, "Protective Clothing Guidelines for Electric Arc Exposure," IEEE, Paper No. PCIC–96–34, pp. 282–298, (1996).

* cited by examiner

Primary Examiner—Yogendra N. Gupta
Assistant Examiner—Derrick G. Hamlin
(74) Attorney, Agent, or Firm—The Maxham Firm

(57) ABSTRACT

Substantially transparent compositions that block electric-arc energy. A process of making the compositions comprise blending an IR/optical dye with a substrate material and subjecting the blend to curing conditions. Products manufactured from the composition ablate upon impact of electric-arc energy.

26 Claims, 1 Drawing Sheet

ELECTRIC-ARC RESISTANT COMPOSITION

BACKGROUND OF THE INVENTION

1. Field of the Invention

The present invention generally relates to electric-arc resistant compositions, and more particularly, to a composition and process for manufacturing electric-arc resistant objects that are at least partially transparent.

2. Discussion of the Related Art

High voltage electrical equipment and other types of electrically powered devices pose a threat of powerful electric arcs or flashes. Electric arcs can occur when an individual is several feet away from the energized equipment. These arcs or flashes may result from short circuits developing from poor electrical grounding, failure of insulation, or by personnel working on or near energized electrical equipment and circuits. Electric arcs have extremely high temperatures of about four times the temperature of the sun's surface and their energy and radiation can result in immediate fatal burns. Firefighters, electric utility workers, factory workers and many other individuals are injured or killed every year from electric arcs.

In recognition of this electric-arc hazard, a wide variety of fabrics for protecting the body and extremities have been developed. Helmets and other types of headgear have also been developed to protect the head from electric arcs. However, little attention has been given to an area of great need—developing a substantially transparent technology that blocks, or absorbs electric arcs.

SUMMARY OF THE INVENTION

The present invention solves the problem of protecting individuals from electric arcs when working around high-voltage devices. Broadly, the present invention provides a composition that can be formed into a wide variety of substantially transparent objects that block electric arcs.

More specifically, one embodiment of the invention is a composition comprising at least one dye that blocks electromagnetic waves in the optical or infrared ranges, or both, and a substrate material. The substrate material and the dye or dyes are proportioned so that the composition ablates upon impact of electric arc energy.

One advantage of the present composition is that it can be formed into a wide variety of substantially transparent barriers that protect users from electric arcs while allowing clear vision through the barrier.

However, the claims alone—not the preceding summary—define the invention.

BRIEF DESCRIPTION OF THE DRAWING

The nature, goals, and advantages of the invention will become more apparent to those skilled in the art after considering the following detailed description when read in connection with the accompanying drawing—illustrating by way of example one product which can be found employing the principles of the invention. The single FIGURE is a perspective view of one embodiment of the composition in the form of a face shield mounted on a helmet.

DETAILED DESCRIPTION OF THE PREFERRED EMBODIMENTS

Definitions

Figure 1:
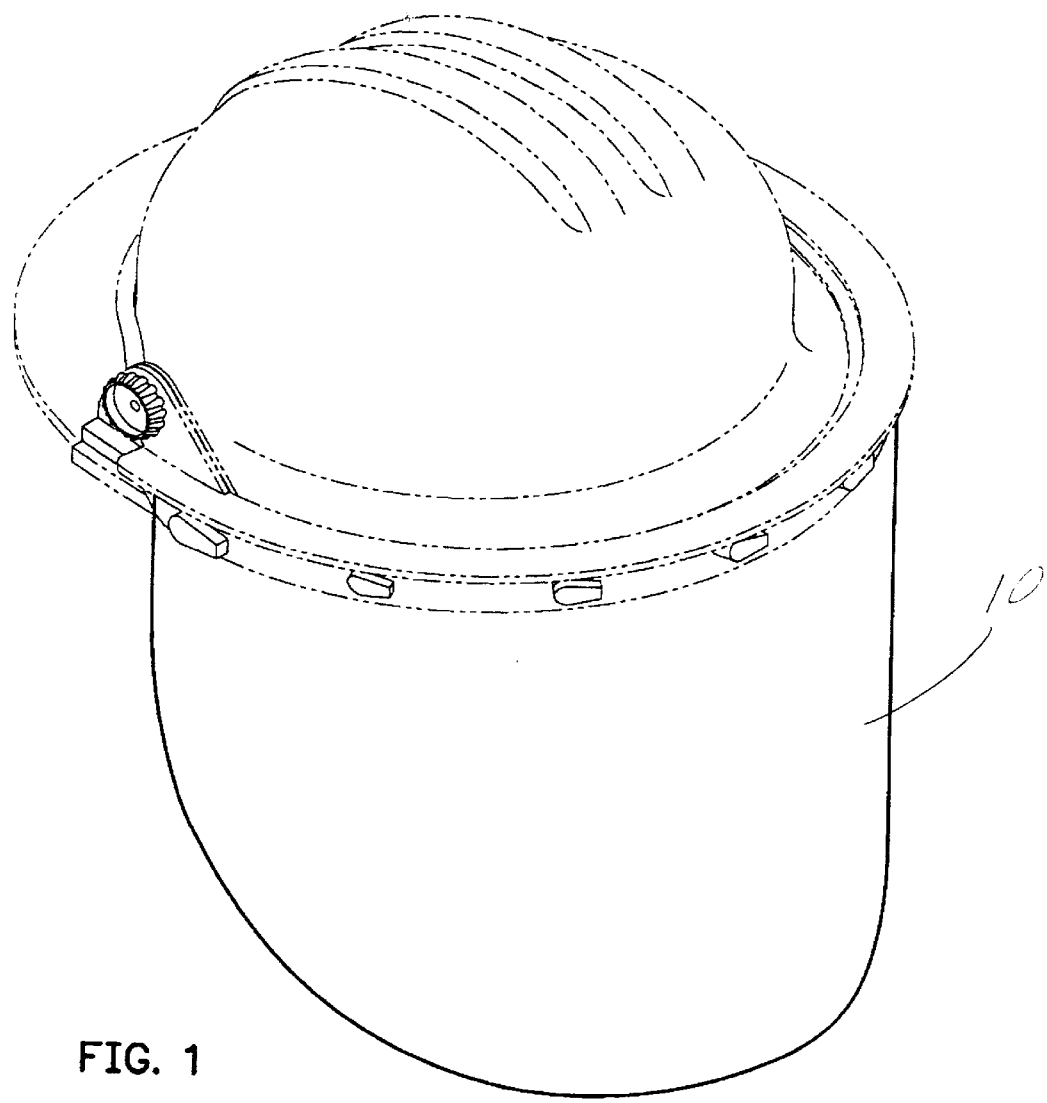

Unless defined otherwise, all technical and scientific terms used herein have the same meaning as is commonly understood by one of skill in the art to which this invention belongs. In event the definition in this section is not consistent with definitions elsewhere, the definitions set forth in this section will control.

As used herein, transparent or substantially transparent refers to a material characteristic that allows the passage of a sufficient amount of light to allow a person looking through the material to view objects under normal working conditions.

As used herein, IR/optical dye is one or more dyes that block at least part of the ultraviolet, or visible, or infrared sections of the electromagnetic wave spectrum.

As used herein, ablate, ablates, or ablation refers to the dissipation of energy by evaporating, vaporizing, or melting.

Composition

Throughout this description, the preferred embodiment and other embodiments should be considered as exemplars, rather than as limitations to the present invention. The composition according to the present invention, when manufactured into products, provides a substantially transparent barrier that protects individuals from electric arcs.

One embodiment of the composition comprises an IR/optical dye blended with a substrate material. The IR/optical dye employed in the composition is comprised of an optical pigment and a separate infrared dye. Preferably, the optical pigment is substantially orange and ideally, the pigment used is Transparent Orange, color number 10017937, manufactured by M.A. Hanna Color of San Fernando, Calif. Alternative optical pigments, or other dyes that block a portion of the visible electromagnetic wave spectrum can also be used.

Preferably a broad spectrum infrared dye is employed, but other infrared dyes may be used. An ideal embodiment of the present invention uses Epolight III-125 Broad Band Infrared Absorption Dye, manufactured by Epolin, Inc., of Newark, N.J.

The substrate, or foundation material is a major constituent of the composition, and preferably is a plastic, or other suitable material. Ideally, the substrate material is Eastman Tenite Propionate 360 Formula—a cellulose acetate-propionate, manufactured by Eastman Chemical of Kingsport, Tenn. Alternative substrate materials may be selected from the families of cellulosics, vinyls, polycarbonates, acrylics and LEXAN (LEXAN is a trademark of the General Electric Company of Schenectady, N.Y.). A more detailed, but not exhaustive, list of alternative foundation, or base materials includes: acrylonitrile-butadiene-styrene, cellulose acetate, cellulose butyrate, ethylene-methyl acrylate, ethylene-vinyl acetate, ionomer, methyl methacrylate/ABS, methacrylate-butydiene-styrene, polyarylate, polycarbonate, polychlorotrifluoroethylene, polycyclohexylene dimethylene terephthalate, polyetherimide, polyethersulfone, polyethylene terephthalate, polyethylene terephthalate glycol comonomer, polymethyl methacrylate, polymethylpentane, polyphthalate carbonate, polysulfone, polyethersulfone, polystyrene, polytetrafluoroethylene, polyurethane, polyvinyl chloride, polyvinylidene chloride, polyvinylidene fluoride, styrene-acrylonitrile, styrene-butadiene styrene, styrene ethylene butylene styrene, silicone, styrene maleic anhydride, styrene, methyl methacrylate copolymer, thermoplastic rubber, polyamide, and TEFLON (TEFLON is a trademark of E.I. du pont de Nemours and Company).

Additional ingredients can be employed in the composition for increasing the durability of the final product, or for helping the individual ingredients to mix together, or to help the composition flow into a manufacturing mold. Dispersants can also be added to the composition to aid in blending the ingredients.

These additional ingredients may include: plasticizers, petroleum derivatives, and lubricants. A preferred embodiment of the composition employs a plasticizer mixed into the substrate material. An ideal embodiment substrate material comprises about 14% plasticizer. The ideal embodiment also uses mineral oil, a petroleum derivative, to help the individual ingredients mix, and zinc stearate, a lubricant, to help the mixture flow during the manufacturing process. The plasticizer may also be employed to facilitate mixing, and improve the flow characteristics of the composition.

One presently preferred composition of the present invention comprises: 0.75 pounds of orange optical pigment; 30 pounds of cellulose acetate-propionate containing 14 percent plasticizer; 22 grams of broad spectrum infrared dye; 2.75 grams of mineral oil; and 10 grams of zinc stearate. Other variations of the composition may change the amount of each ingredient, or substitute specific ingredients. With the specific composition identified above, functionally effective ranges, or an operative amount, of the components may be easily determined by one of ordinary skill in this technical field.

Product

The composition of the present invention provides a level of protection from electric-arc energy previously thought unachievable with transparent products. It is believed that the invention first blocks the harmful portion of the electromagnetic spectrum, while almost simultaneously absorbing the electric arc energy by ablation. As the ablation continues, the amount of protection increases, as the product becomes more opaque to the energy. It has also been theorized that the ingredients of the composition synergistically combine to achieve these extraordinary results.

The composition described above is processed into products by blending the ingredients together and subjecting the blend to curing conditions. The curing may take place in an injection mold, or other suitable apparatus. The curing may comprise heating the mixture to a specific temperature, before or during or after, a shape-forming process like molding, compressing or the like. Alternatively, curing may comprise adding a catalyst to the composition, causing the ingredients to harden so that they can maintain a constant shape.

An envisioned, but by no means complete, list of products manufactured from the composition can include: face shields, multi-layered face shields, barriers, multi-layered barriers, screens, multi-layered screens, windows, multi-layered windows, eyewear and multi-layered eyewear.

One example of an envisioned face shield product is illustrated in the FIGURE. Face shield 10 is attached to a hard hat or other type of headgear and protects users from electric arcs while at the same time allowing the user to view objects under normal lighting conditions. Alternative embodiments of the face shield, or other products, can have an anti-fog coating to prevent fogging of the product. An ideal embodiment would also be dielectric, that is, a non-conductor of electricity.

One embodiment of a face shield made of the composition of the present invention blocks the electromagnetic wave spectrum from about 200 nanometers (nm) to about 500 nm, and from about 800 nm to about 1800 nm. In other words, the face shield is permeable to electromagnetic waves ranging from about 500 nm to about 800 nm. A face shield so constructed having a thickness of about 0.070 inches, can absorb up to about 40 calories per square centimeter. Alternative embodiments may be thinner or thicker, and may comprise one or more layers of material, with or without gaps between the layers. Other embodiments may block, or be permeable to, different parts of the electromagnetic wave spectrum.

A preferred embodiment face shield made of the above-described composition allows about 45% of 600 nm frequency light to pass through to the user. Other embodiments may be permeable to more or less light, to suit various tasks performed by users employing the product.

OTHER EMBODIMENTS

Certain preferred embodiments have been described above. It is to be understood that a latitude of modification and substitution is intended in the foregoing disclosure, and that these modifications and substitutions are within the literal scope—or are equivalent to—the claims that follow.

Accordingly, it is appropriate that the following claims be construed broadly and in a manner consistent with the spirit and scope of the invention herein described.

What is claimed is:

1. A composition comprising:
    a first dye that blocks electromagnetic waves in at least one of the following regions: visible and infrared; and
    a substrate material, the substrate material and the first dye being chosen and blended in proportion so that the composition is at least substantially transparent and ablates upon impact of electric energy.

2. The composition according to claim 1, wherein the composition also blocks electromagnetic waves.

3. The composition according to claim 2, wherein the electromagnetic waves blocked range from about 200 nm to about 500 nm.

4. The composition according to claim 2, wherein the electromagnetic waves blocked range from about 800 nm to about 1800 nm.

5. The composition according to claim 1, wherein the first dye blocks a portion of the visible electromagnetic wave spectrum.

6. The composition according to claim 1, and further comprising a second dye, wherein the second dye blocks a portion of the infrared electromagnetic wave spectrum, and the first dye blocks a portion of the visible electromagnetic wave spectrum.

7. The composition according to claim 1, wherein the first dye blocks a portion of the infrared electromagnetic wave spectrum.

8. The composition according to claim 1, and further comprising a second dye, wherein the second dye blocks a portion of the visible electromagnetic wave spectrum, and the first dye blocks a portion of the infrared electromagnetic wave spectrum.

9. The composition according to claim 1, wherein the substrate material is selected from the group consisting of cellulosics, vinyls, polycarbonates and acrylics.

10. The composition according to claim 1, and further comprising a plasticizer.

11. The composition according to claim 1, and further comprising a petroleum derivative.

12. The composition according to claim 1, and further comprising a lubricant.

13. The composition according to claim 1, wherein the composition is formed into a product.

14. A composition resistant to an electric-arc comprising:
    an infrared/optical dye; and
    a substrate material, the infrared/optical dye and substrate material being chosen and blended in proportion so that the composition is at least substantially transparent, blocks electromagnetic waves and ablates when struck by radiation from an electric arc.

15. The composition according to claim 14, wherein the infrared/optical dye is selected from at least one of the group consisting of optical dyes and infrared dyes.

16. The composition according to claim 14, wherein the infrared/optical dye is substantially orange.

17. The composition according to claim 14, wherein the substrate material is a cellulose acetate-propionate.

18. The composition according to claim 14, and further comprising a plasticizer.

19. The composition according to claim 14, and further comprising a dispersant.

20. The composition according to claim 19, wherein the dispersant is a petroleum derivative.

21. The composition according to claim 14, and further comprising a lubricant.

22. The composition according to claim 21, wherein the lubricant is a zinc stearate.

23. The composition according to claim 14, wherein the composition is formed into a product.

24. The composition according to claim 23, wherein the product is selected from the group consisting of at least face shields, multi-layered face shields, barriers, multi-layered barriers, screens, multi-layered screens, windows, multi-layered windows, eyewear and multi-layered eyewear.

25. A process for producing an electric-arc resistant composition comprising:

blending an infrared/optical dye with a substrate material; and subjecting the blend to curing conditions, wherein the product is at least substantially transparent.

26. A product formed by the process of claim 25.

* * * * *

UNITED STATES PATENT AND TRADEMARK OFFICE
CERTIFICATE OF CORRECTION

PATENT NO. : 6,375,865 B1
DATED : April 23, 2002
INVENTOR(S) : Roy V. Paulson et al.

It is certified that error appears in the above-identified patent and that said Letters Patent is hereby corrected as shown below:

<u>Title page,</u>
Item [54], Title, should read -- ELECTRIC-ARC FLASH RESISTANT COMPOSITION --.

Signed and Sealed this

Twenty-ninth Day of November, 2005

JON W. DUDAS
*Director of the United States Patent and Trademark Office*

(12) EX PARTE REEXAMINATION CERTIFICATE (7753rd)
United States Patent
Paulson et al.

(10) Number: US 6,375,865 C1
(45) Certificate Issued: Sep. 21, 2010

(54) ELECTRIC-ARC FLASH RESISTANT COMPOSITION

(75) Inventors: Roy Victor Paulson, Temecula, CA (US); Elihu Hoagland, IV, Louisville, KY (US)

(73) Assignee: Paulson Manufacturing Corporation, Temecula, CA (US)

Reexamination Request:
No. 90/010,083, Jan. 29, 2008

Reexamination Certificate for:
Patent No.: 6,375,865
Issued: Apr. 23, 2002
Appl. No.: 09/372,371
Filed: Aug. 11, 1999

Certificate of Correction issued Nov. 29, 2005.

(51) Int. Cl.
*H01B 1/00* (2006.01)

(52) U.S. Cl. .............................. 252/500; 8/506; 8/637.1; D29/108; D29/109; D29/110; 2/410; 2/426; 2/424; 2/431; 2/434

(58) Field of Classification Search ....................... None
See application file for complete search history.

(56) References Cited

U.S. PATENT DOCUMENTS

| 3,382,183 | A | | 5/1968 | Donoian et al. | |
|---|---|---|---|---|---|
| 4,170,690 | A | * | 10/1979 | Armbruster et al. | .......... 428/447 |
| 4,645,796 | A | * | 2/1987 | Beyer et al. | .................. 525/84 |
| 5,312,857 | A | * | 5/1994 | Sullivan | .................... 524/400 |
| 5,400,175 | A | * | 3/1995 | Johansen et al. | ............ 359/361 |

OTHER PUBLICATIONS

Avallone et al., Mark's Standard Handbook for Mechanical Engineers, 1987, pp. 6–174–6–175, 13–26–13–38, McGraw–Hill book Company, Ninth Edition.
Brydson, Plastics Materials, 1975, pp. 112–113, The Butterworth Group, Third Edition.

* cited by examiner

*Primary Examiner*—Brenda Brumback

(57) ABSTRACT

Substantially transparent compositions that block electric-arc energy. A process of making the compositions comprise blending an IR/optical dye with a substrate material and subjecting the blend to curing conditions. Products manufactured from the composition ablate upon impact of electric-arc energy.

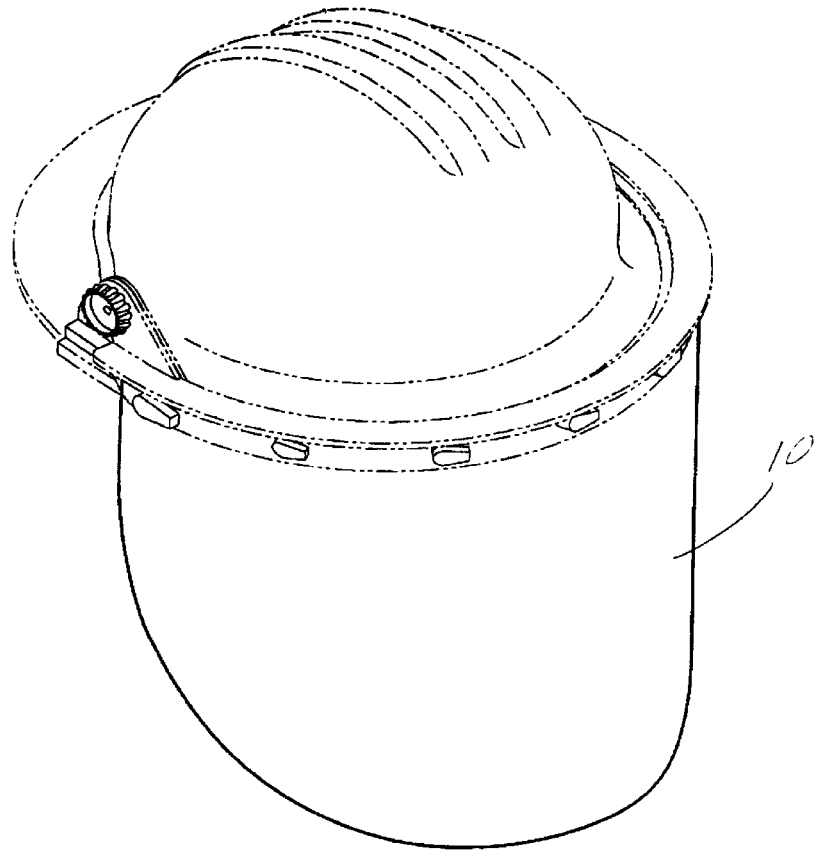

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 4, 14 and 25 are determined to be patentable as amended.

Claims 2, 3, 5-13, 15-24 and 26, dependent on an amended claim, are determined to be patentable.

New claims 27-35 are added and determined to be patentable.

1. A composition comprising:
   a first dye that blocks electromagnetic waves in at least one of the following regions:
   visible and infrared; and
   a substrate material, the substrate material and the first dye being chosen and blended in proportion so that the composition is at least substantially transparent and ablates upon impact of [electric] *electric-arc* energy, *and so that the composition effectively protects against injury to a human body from the electric-arc energy*.

4. The composition according to claim 2, wherein the electromagnetic waves *are* blocked [range from] *through the spectrum of* about 800 nm to about 1800 nm.

14. A composition resistant to an electric-arc comprising:
    an infrared/optical dye; and
    a substrate material, the infrared/optical dye and substrate material being chosen and blended in proportion so that the composition is at least substantially *visually* transparent, blocks electromagnetic waves and ablates when struck by radiation from an electric arc, *so that the composition effectively protects against injury to a human body from the electric arc*.

25. A process for producing an electric-arc resistant composition comprising:
    blending an infrared/optical dye with a substrate material; and
    subjecting the blend to curing conditions[.]*;*
    wherein the product is at least substantially transparent[.]*;* *and*
    *wherein the electric-arc resistant composition ablates when struck by radiation from an electric arc, so that the composition effectively protects against injury to a human body from the electric arc.*

27. *An electric-arc shield manufactured from a composition, said composition comprising:*
    *a first dye that blocks electromagnetic waves in at least one of the following regions: visible and infrared; and*
    *a substrate material, the substrate material and the first dye being chosen and blended in proportion so that the shield is at least substantially transparent and ablates upon impact of electric-arc energy, and so that the shield effectively protects against injury to a human body from the electric-arc energy.*

28. *The electric-arc shield according to claim 27, wherein the shield also blocks electromagnetic waves.*

29. *The electric-arc shield according to claim 27, wherein the first dye blocks at least a portion of the visible electromagnetic spectrum.*

30. *The electric-arc shield according to claim 27, and further comprising a second dye, wherein the second dye blocks at least a portion of the infrared electromagnetic wave spectrum and the first dye blocks at least a portion of the visible electromagnetic wave spectrum.*

31. *An electric-arc shield resistant to an electric-arc manufactured from a composition comprising:*
    *an infrared/optical dye; and*
    *a substrate material, the infrared/optical dye and substrate being chosen and blended proportion so that the shield is at least substantially transparent, blocks electromagnetic waves and ablates when struck by radiation from an electric arc, so that the shield effectively protects against injury to a human body from the electric-arc energy.*

32. *The electric-arc shield according to claim 31, wherein the infrared/optical dye is selected from at least one of the groups consisting of optical dyes and infrared dyes.*

33. *The electric-arc shield according to claim 31, wherein the infrared/optical dye is substantially orange.*

34. *The electric-arc shield according to claim 31, wherein the substrate material is a cellulose acetate-propionate.*

35. *A process for producing an electric-arc resistant electric-arc shield comprising:*
    *preparing an electric-arc resistant composition by blending an infrared/optical dye with a substrate material; and*
    *manufacturing an electric-arc resistant shield from said electric-resistant composition wherein the electric-arc shield is at least substantially visually transparent; and*
    *wherein the electric-arc resistant composition ablates when struck by radiation from an electric arc, so that the shield effectively protects against injury to a human body from the electric energy.*

* * * * *